United States Patent
Orszulak et al.

(12) 
(10) Patent No.: US 6,685,701 B2
(45) Date of Patent: Feb. 3, 2004

(54) SMART RECOGNITION APPARATUS AND METHOD

(75) Inventors: James Henry Orszulak, Nederland, CO (US); Gary Lee Dobbins, Jr., Longmont, CO (US)

(73) Assignee: Sherwood Services AG, Norwalk, CT (US)

( * ) Notice: Subject to any disclaimer, the term of this patent is extended or adjusted under 35 U.S.C. 154(b) by 35 days.

(21) Appl. No.: 10/166,500

(22) Filed: Jun. 10, 2002

(65) Prior Publication Data

US 2003/0014043 A1 Jan. 16, 2003

Related U.S. Application Data

(63) Continuation of application No. 09/528,380, filed on Mar. 17, 2000, now Pat. No. 6,402,743, which is a continuation of application No. 08/988,362, filed on Dec. 10, 1997.

(51) Int. Cl.[7] .............................................. A61B 18/04
(52) U.S. Cl. ........................... 606/34; 606/41; 607/101
(58) Field of Search ........................... 606/1, 4, 10–12, 606/34, 37, 41–52; 607/1, 98, 100–102, 115

(56) References Cited

U.S. PATENT DOCUMENTS

| | | | |
|---|---|---|---|
| 5,157,603 A | | 10/1992 | Scheller et al. |
| 5,209,235 A | * | 5/1993 | Brisken et al. ............. 600/466 |
| 5,342,356 A | | 8/1994 | Ellman et al. |
| 5,396,062 A | | 3/1995 | Eisentraut et al. |
| 5,400,267 A | | 3/1995 | Denen et al. |
| 5,413,573 A | | 5/1995 | Koivukangas |
| 5,434,398 A | | 7/1995 | Goldberg |
| 5,605,150 A | | 2/1997 | Radons |
| 5,625,370 A | | 4/1997 | D'Hont |
| 5,651,780 A | | 7/1997 | Jackson et al. |
| 5,660,567 A | | 8/1997 | Nierlich |
| 5,693,042 A | * | 12/1997 | Boiarski et al. ............. 606/10 |
| 6,053,871 A | * | 4/2000 | Cockburn ................... 600/459 |
| 6,068,627 A | | 5/2000 | Orszulak et al. |
| 6,402,743 B1 | | 6/2002 | Orszulak et al. |

FOREIGN PATENT DOCUMENTS

WO     WO 9608794     3/1996

\* cited by examiner

*Primary Examiner*—Roy D. Gibson

(57) ABSTRACT

A qualifying connection for an instrument attaches to a source of electrosurgery energy and to the instrument and has first and second parts coupled to the instrument and the source, respectively. Optical couplings on the connection transmit invisible energy to identify the instrument and are proximate on the first and second parts. A light modifier on the first part is proximal to the second part for modification of radiation in the infrared wavelengths so infrared transmitters encode signals and non-contact coded proximity detectors on the second part are the coupled detectors. Mechanical attachments include conjugating male and female portions which physically extend between the parts and matingly engage. An identifying circuit couples to the second part and responds to invisible light optically communicated across the couplings for verifying the type of instrument connected by the cable to the source. A method of using the connection has steps including juxtaposing and conjugating the parts with attachments and couplings for transmitting invisible optical energy to identify the instrument. The method includes modifying the invisible optical energy with geographically disposed proximate couplings of the parts when the attachments engage and the couplings are proximate. Passing and assessing signals of the modified energy are transmitted through the connection and to an identifying circuit in the source.

12 Claims, 2 Drawing Sheets

SMART RECOGNITION APPARATUS AND METHOD

CROSS REFERENCE TO RELATED APPLICATIONS

This application is a continuation of U.S. application Ser. No. 09/528,380 filed on Mar. 17, 2000 now U.S. Pat. No. 6,402,743 by Orszulak et al. entitled "SMART RECOGNITION APPARATUS AND METHOD" which is a continuation of U.S. patent application Ser. No. 08/988,362 filed on Dec. 10, 1997 by Orszulak et al. entitled "SMART RECOGNITION APPARATUS AND METHOD", the entire contents of both of these applications are incorporated by reference herein.

FIELD OF THE INVENTION

This relates to a smart recognition system for electrosurgery and a qualifying connection with non contact, coded proximity detection, using diffuse surface, infrared reflective coupling as an instrument identification process. More particularly, the system identifies, qualifies or verifies the correct connection between a source of high frequency energy and an instrument.

BACKGROUND OF THE DISCLOSURE

Electrosurgery requires controlled application, with an instrument, of radio frequency energy to an operative tissue site. To achieve successful clinical results during surgery, the electrosurgical generator, as the source of the high frequency or radio frequency energy, should be mated correctly with an appropriate instrument for a specific surgery. Due to the variety of operative electrosurgical procedures requiring various levels of radio frequency energy delivery from an attached instrument, problems arise with mismatching an electrosurgical generator and the instrument. The operating rooms with a variety of instruments and generators available for surgery create a potential for mismatch problems and thus may increase the patient risk.

U.S. Pat. No. 5,400,267 discloses a system with a non volatile memory with an EEPROM in the instrument or its attached cable. The memory identifies the instrument. A problem arises when the memory is located external to the power supply requiring hardwire connections. The communicated data transmission from the memory to the control may have an error due to radiated emissions from radio frequency energy wires located closely when delivered by the electrosurgical generator during surgery. Radio frequency exposure will interfere with the identification information being transmitted so it becomes difficult to determine that the correct medical instrument is attached to the power source. In addition a further problem is presented because the memory means must be located in the reusable part of the medical instrument. For purposes of instrument identification, this patent restricts application to reusable medical instruments and prohibits an instrument identification for low cost disposables.

U.S. Pat. No. 5,413,573 describes identification of surgical instruments by incorporating a unique interface between two components such that their engagement by two surfaces defines the identity of an instrument if properly mated. In this system, a switch is provided on a component first surface called the orientation means. A second surface incorporates a contact on an intermediate component. Upon engagement of these two components the appropriate switch and contact mating establish the given identity. A problem arises with this approach, as the integrity of the identity depends on the engagement with the mating of components. A degradation of this identification occurs, with repeated engagements causing deterioration of the mating switch to contact interface between components. A secondary problem also occurs from the multiple engagement process as this approach requires a specific orientation alignment between mating surfaces. As the numbers of switch to contact interfaces increase, a tighter tolerance must be maintained between mating surfaces to retrieve the identity information. Repeated component engagements will also deteriorate this orientation alignment and thus degrade the accuracy in maintaining the identity.

U.S. Pat. No. 5,434,398 uses a magnetic encoding process to establish the identity with a card based system. Modulated magnetic fields embedded in a smart card require the use of a ferromagnetic element to retain the unique identity code. A magnetic reader decodes the card information allowing system activation. Exposure of this system to radio frequency energy used in electrosurgery, could effect the integrity of the magnetic smart card and degrade the ability of the magnetic based card reader to accurately decode its proper identity. Radio frequency energy would remagnetize both the smart card and reader by induced magnetic coupling to the ferromagnetic elements. Clearly this system would require magnetic shielding to retain identity data. Indeterminate magnetic sources present in the operating room also creates additional major problems for this system and would make its use in electrosurgery suspect.

U.S. Pat. No. 5,396,062 describes a power source receptacle system with detection of the presence of a mated plug, by using an optical coupling technique, established by beam passage through the receptacle. This approach uses a light emitter to generate a beam, that passes through openings in the receptacle contacts, to a receiver aligned on a dedicated optical axis. A powered instrument having a bladed plug for insertion in a receptacle breaks the beam transmission path sending a corresponding signal to a controller that detects the plug engagement. The '062 patent is limited in use, in that, it provides for detection when a mating plug is either inserted or removed from the receptacle. Power can only be activated or deactivated in the receptacle, based on whether the mating plug is engaged or disengaged. Numerous problems are presented by this system. First, the identity is not recognized or associated to a given instrument plugged into the receptacle. Second, the power applied to the receptacle cannot be differentiated between specific pluggable instruments. Also, additional problems are presented, because a specific optical axial alignment is required for beam passage, through the openings in the power receptacle contacts, thereby requiring a specific mechanical alignment integrity.

U.S. Pat. No. 5,625,370 has an electromagnetic device and method in an identification system apparatus. An electrically conductive material is disposed to pass through a magnetic flux loop of the electromagnetic device. The coupling established between those components is the means by which identification information is transferred. An antenna may also be electrically connected to the conductive material to augment the apparatus for receiving transmitted identification information. Multiple identification problems exist with radio frequency based equipment due to radiation coupling with the electromagnetic conductive strip and antenna which will deteriorate the identity signals. Error borne signals lose their identity and become inaccurate with decoding. The radio frequency energy may also electromagnetically couple to distort the magnetic flux loop of the electromagnetic device. This will reduce the signal to noise ratio during information transfer and lower the accuracy of the identity information recovered.

International Patent WO9608794 has a security code identification circuit that uses a radio frequency based card reader and decoder method to recover a digital security code. The card reader includes a receiving antenna sensitive to a signal generated to an access card. A receiver circuit is coupled to the receiving antenna to detect and process an analog signal that is then converted to a digital security code. A problem with this type of recognition system makes it error borne and unacceptable for code identification in radio frequency systems. Radio frequency energy contains components that will be picked up and coupled by the reader receiving antenna as it is sensitive to those frequencies. This will confuse the card reader antenna and detector electronics. Erroneous signal components will be processed along with the identification signal; thus, generating errors in the detected signal. The recognition system digital security code could not be a true representation of the signal information and thus identification is inaccurate for use with radio frequency based equipment.

U.S. Pat. No. 5,660,567 has a smart connector for a sensor with removable encoding medical device. The smart identification method is accomplished within the connector module pin interconnect wherein a dedicated group of removable pins from a multiple pin connector are used to attach an encoding device read by the sourcing equipment. The sensor, attached to this connector with encoding device, identifies the medical device. The smart connector distinguishes either a resistor, an electronic device, a memory device or a modulating device to identify the medical device. Insertion and removal of an encoder requires assembly, thereby making the accuracy and repeatability of the identification process suspect and prone to error. Recovery of the smart signal interface is dependent on the reliability of the electrical and mechanical connections required as mechanical misregistration and intermittent electrical contacts will degrade accuracy. In applications where radio frequency energy exists proximate to the encoding, the corruption of electronic signals used for identity recognition will result. Radio frequency energy will radiate and conductively couple with electronic or memory devices to reduce the accuracy of decoded signals.

U.S. Pat. No. 5,651,780 has an identification and monitoring method for recognizing the physical and or functional characteristics of medical devices. Identification means located within the medical instrument uses an electronic memory such as a non-volatile RAM, ROM, EEPROM or EPROM. Information is stored about the medical device attributes in look-up tables within a power source include an acceptable device list or performance characteristic to compare to the attached instrument to determine application use. The identification teachings of this patent are similar to the one identified in U.S. Pat. No. 5,400,267. The problems with '780 are similar to those mentioned for the '267 patent.

A solution to the above problems is disclosed and claimed herein and it addresses the noted limitations of the patents discussed. A smart recognition system for electrosurgery includes a smart connector sensing topology. In addition to uniquely recognizing the correct mating of electrosurgical power sources with the attached pluggable medical instruments the smart connector sensing approach herein provides a solution that has inherent immunity to the problems discussed. The present system has the smart identification code integral to the connector assembly to avoid assembly errors. Use of a non-contact, optical method smart signal recovery eliminates electrical contact degradation and mechanical misalignment problems. An infrared diffuse reflectance code identification recovery method which has inherent accuracy and reliability in harsh, high power radio frequency electrosurgical environments and application in fields outside electrosurgery.

SUMMARY OF THE INVENTION

The preferred embodiment of the smart connector sensing approach has a non-contact, coded proximity detector that uses a diffuse surface, infrared reflective coupling. Delineation of this smart sense topology yields benefits providing the immunity referenced as an intrinsic property of the means used. A non contact technique avoids problems associated with mechanical alignment, component engagement and part mating orientation. Physical contact for sensing between mating components is not required for identity recognition. Coded proximity detection provides a unique identity association between plugged medical instruments and Rf energy sources. Multiple integrated optical paths, each containing both emitting and receiving components, proximally detect a unique Nth bit code identification for each medical instrument, plugged into an Rf energy source. Identification problems, associated with memory communication and data storage and registration and fatigue problems caused by component engagement alignment problems of multiple sensors for code identity, are avoided.

A light coupled, non-magnetic approach, avoids instrument identity problems with electromagnetic (EMI) interference. Light coupled identity sensing is immune to this noise. A light coupled technique, also avoids problems caused by electrical discontinuity, due to a mechanical disconnection of wire contacts between hardwire connections, or switches. A diffuse surface reflective coupling, avoids problems associated with optical axial alignment and focused optics. Unfocused optical components are preferred to proximally detect plugged instruments with diffuse surface reflection. Optimal smart sense recognition is obtained from non-planer, diffuse surface, including medical instrument plugs located within a proximal range from the smart sense components. As a result, tight optical and mechanical registration tolerances, along with high polished optical surfaces are not required to maximize instrument recognition and signal recovery.

Infrared reflective coupling is preferred as it provides high accuracy sensing and signal recovery for smart recognition, medical instrument detection. Unlike the visible light sensors, that encompass a broad spectrum of light wavelengths, infrared light exists at a narrow band width wavelength. This provides a high accuracy, sensory signal recognition apparatus and method. Infrared offers a high discriminating signal to noise ratio between the smart sense light source and the ambient background light of the operating room. A smart connector sensing approach has maximum flexibility for medical instruments. Disposable and reusable medical instruments, may be uniquely identified and attached to an electrosurgical Rf generator source, for clinical use. A smart recognition system for electrosurgery is herein presented. The benefits described are unique medical applications for electrosurgery. In addition, the approaches for applications outside electrosurgery are possible as example: lasers, microwaves, ultrasonics and fluid based energy delivered systems.

The smart recognition system for electrosurgery provides an accurate medical instrument identification, for instruments attached to an electrosurgical generator source of high frequency electrosurgical energy. A control of the application of Rf energy during surgical procedures is also disclosed. Specific Rf power levels developed in the electrosurgical generator may be uniquely activated and coupled to individually recognized medical instruments for performing electrosurgery. Activation and surgical use of the Rf energy source are only allowed with an appropriate validation from the smart recognition system. This occurs when the proper medical instrument has been attached to the electrosurgical generator. Using this approach to control the power source for a particular tissue and to achieve the desired clinical effect prevents misapplication of Rf energy to the patient. As a result, the risk of patient injury is minimized and safety increased.

DETAILED DESCRIPTION OF THE INVENTION

Figure 1:
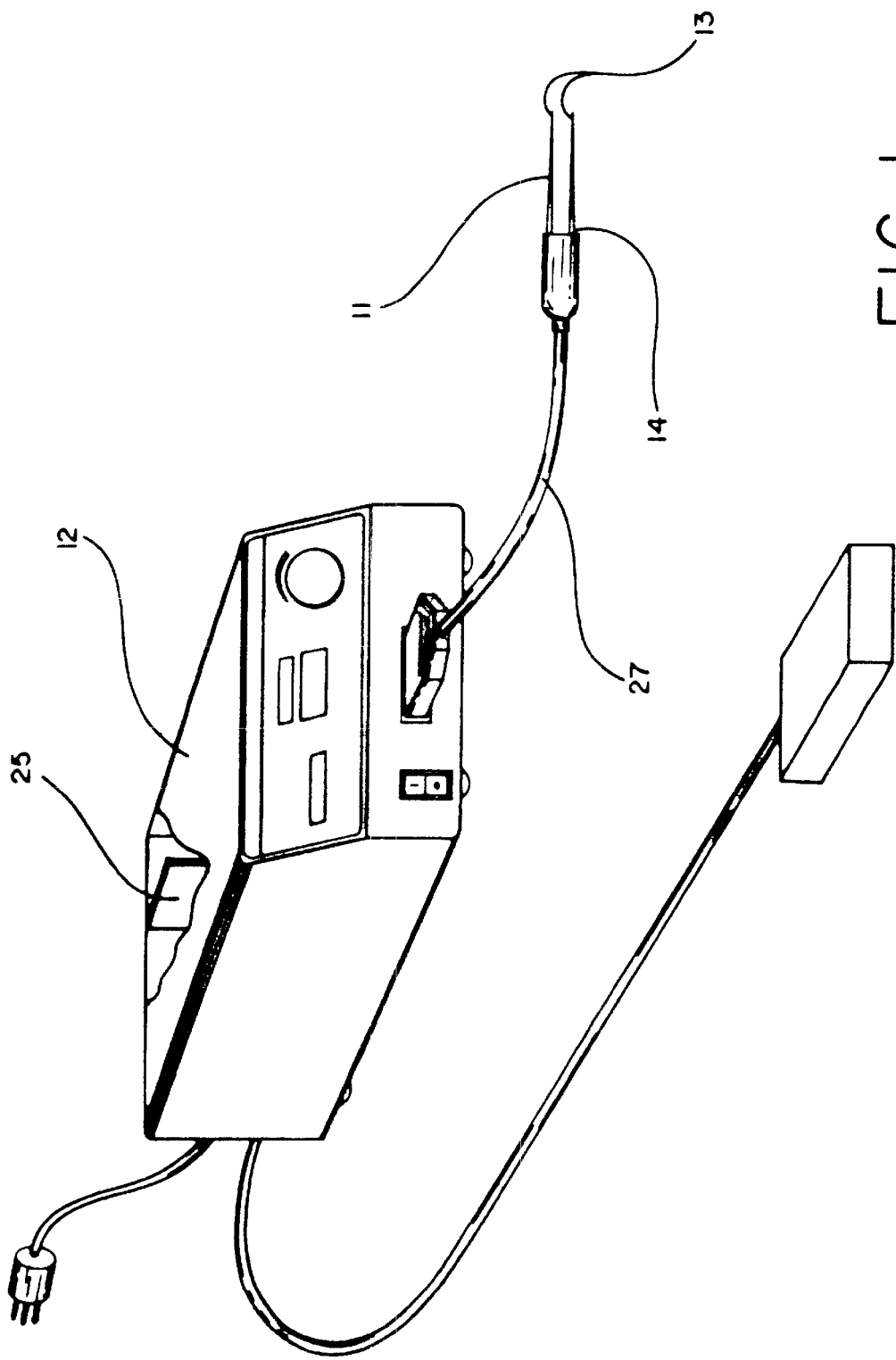
FIG. 1 is a perspective view of the smart recognition system with a source of medical treatment, a qualifying connection and attached instrument.

A qualifying connection 10 is disposed between an instrument 11 and a source of medical 12 treatment for passage of treatment energy from the source of medical treatment 12 through the qualifying connection 10 to the instrument 11 and to a patient. The qualifying connection 10 selectively permits passage of information from the instrument 11 to the source of medical treatment 12 in FIGS. 1 and 2. The qualifying connection 10 includes the instrument 11 having a distal end 13 for treatment of the patient and a proximal end 14 for manipulation by a surgeon. The instrument 11 is connected to the qualifying connection 10. The source of medical treatment 12 provides energy delivery to the instrument 11. The source of medical treatment 12 is attached to the qualifying connection 10. A first part 15 of the qualifying connection 10 connects to the instrument 11 in FIG. 2. A second part 16 of the qualifying connection 10 is carried on and connected to the source of medical treatment 12. Optical couplings 17 and 18 on the qualifying connection 10 extend between the first and second parts 15 and 16 respectively to pass optical energy thus communicating information in the form of the identity of the instrument 11 to the source of medical treatment 12.

Figure 2:
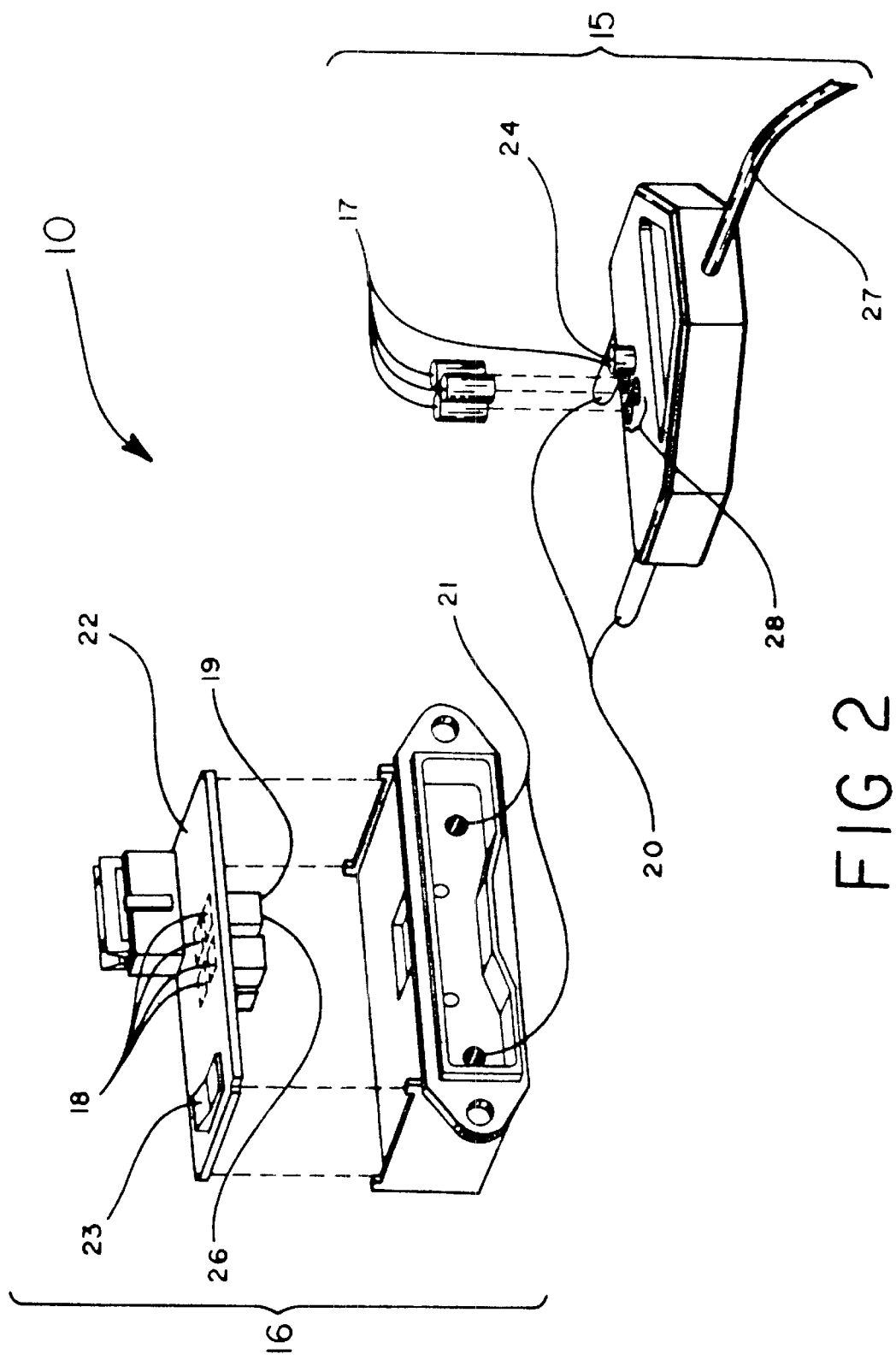
FIG. 2 is a side view of the connector of FIG. 1 enlarged and in cross section for showing the relative relationships of the optical couplings and the mechanical attachments of first and second parts of the qualifying connection.

A light supply 19 is in the source of medical treatment 12 is part of the qualifying connection 10 for transmitting across the communicating optical couplings 17 and 18 shown in FIG. 2. The light supply 19 operates within a predetermined wavelength. Mechanical attachments 20 and 21 across the qualifying connection 10 juxtaposition the first and second parts 15 and 16 thereof. The mechanical attachments 20 and 21 have geometric mechanical conjugations for delivering medical treatment through the qualifying connection 10 from the source of medical treatment 12 to the instrument 11. The mechanical attachments 20 and 21 position geographically the optical couplings 17 and 18 in proximity to communicate between the first part 15 on the instrument 11 and the second part 16 on the source of medical treatment 12 when the mechanical attachments 20 and 21 conjugate so the optical couplings 17 and 18 may communicate the information as an indication of the identity of the instrument 11 connected to the source of medical treatment 12.

An identifying circuit 22, a circuit board in the source of medical treatment 12 and on the second part 16 responds to the information as the indication of light optically communicated through the optical couplings 17 and 18 thereby differentiating the type of instrument 11 connected by the mechanical attachments 20 and 21 through the qualifying connection 10 to the source of medical treatment 12. The identifying circuit 22 in FIG. 2 signals verification to the source of medical treatment 12. A switch 23, preferably a comparator integrated circuit, is connected to the identifying circuit 22 in the source of medical treatment 12. The switch 23 responds to the signaling of the identifying circuit 22. The switch further connects within the source of medical treatment 12 for enabling the passage of medical treatment 12 from the source of medical treatment 12 through at least one of the mechanical attachments 20 or 21 and to the instrument 11.

Conjugating male and female portions may be one form of the mechanical attachment 20 and 21 as shown in FIG. 2. The male and female portions physically extend between the first and second parts 15 and 16 across the qualifying connection 10 for mating engagement. The optical couplings 17 and 18 positioned on the first and second parts 15 and 16 are preferably aligned in proximate relation for communication therebetween upon the mating engagement of the mechanical attachments. The optical coupling 17 on the first part 15 includes a light modifier 24. The light modifier 24 includes either a diffuse surface, a coating, a matrix of holes or a preselected light responsive material to modify the wavelength of radiation affected by the light modifier 24 for thereafter receipt by the optical coupling 18 on the second part 16 for signaling the source of medical treatment 12, see FIG. 2.

The mechanical attachments 20 and 21 include one or more male portions on the first part 15 for conjugation. The mechanical attachments 20 and 21 include one or more female portions on the second part 16 for conjugation. Of course the male and female portions could be reversed or alternated. The first part 15 of the optical couplings 17 and 18 includes the light modifier 24 indicative of the type of instrument 11 connected to the first part 15. Infrared transmitters as a preferred light supply 19 are positioned on the second part 16 proximal the light modifier 24 for optical communication of the light therethrough. The source of medical treatment 12 is preferably a source of high frequency energy, but could be a laser, hydro disector, aspiration or other medical or surgical delivery system. A memory 25 with the source of medical treatment receives the information as the indication in the form of modified light energy from the optical couplings 17 and 18 best shown in FIG. 1. The memory 25 compares the light transmitted through the optical couplings 17 and 18 modified thereby with information. The memory 25 receives the information and controls the activation or deactivation of the energy source 12. The optical couplings 17 and 18 preferably include a diffuse surface infrared reflector as the preferred light modifier 24 on the first part 15 and non contact coded proximity detectors 26 as part of the light supply 19 on the second part 16 responsive to the light returned from the diffuse surface infrared reflector 24 communicated as information indicative of the instrument 11 identification for the identifying circuit 22.

A method of using the qualifying connection 10 for the instrument 11 attached to source of high frequency energy 12 for electrosurgery and for delivering surgical signals from the source of high frequency energy 12 through the qualifying connection 10 to and from the instrument 11 has first and second parts 15 and 16. The method has steps including juxtapositioning the first and second parts 15 and 16 across the qualifying connection 10 with mechanical attachments 20 and 21 and optical couplings 17 and 18 therebetween. Conjugating the first and second parts 15 and 16 on the qualifying connection 10 with geometric mechanical attachments 20 and 21 and transmitting invisible optical energy across optical couplings 17 and 18 juxtaposed by first and second parts 15 and 16 of the qualifying connection 10 for communicating instrument 11 identity with invisible light supplied from the source of high frequency energy 12 are steps of the method. The method has the step of modifying the invisible optical energy with geographically disposed proximate optical couplings 17 and 18 of the first and second parts 15 and 16 when the mechanical attachments 20 and 21 engage so the optical couplings 17 and 18 are proximate. Communicating the type of instrument 11 connected by a cable 27 between the first part and the instrument 11, by passing a signal of the modified invisible optical energy through the qualifying connection 10 and to identifying circuit 22 in the source of high frequency 12 is a method step. A step of the method is assessing the modified invisible optical energy from the optical couplings 17 and 18 with the identifying circuit 22 for use as verification for controlling the source of high frequency energy 12. A method step is enabling the flow of high frequency energy 12 from the source of high frequency energy 12 through at least one of the mechanical attachments 20 or 21, the cable 27 and to the instrument 11 with switch 23 in the source of high frequency energy 12 responsive to control from the identifying circuit 22. Carrying high frequency energy through the mechanical attachments 20 and 21 from the source of high frequency energy 12 to the instrument 11 and through cable 27 between the first part 15 of the qualifying connection 10 and the instrument 11 is a step.

The method has a step of conjugating male and female portions that form the mechanical attachments 20 and 21 by physically extending the mechanical attachments 20 and 21 between the first and second parts 15 and 16 across the qualifying connection 10 during mating engagement. The method includes the step of communicating between the optical couplings 17 and 18 by transmitting optical energy as signals from the second part 16 as encoded in modified invisible optical energy by light modifier 24 on the first part 15 sensed by detectors 26 on the second part 16 positioned proximate by the mating engagement of the mechanical attachments 20 and 21. The method has the step of modifying invisible light radiation in the infrared wavelengths by a diffuse surface as the light modifier 24. The method includes the step of modifying the invisible light radiation with a matrix 28 on the first part and infrared emitters on the second part positioned proximate to the matrix 28 for coding signals. The matrix 28 is preferably a combination of diffuse reflectors and holes in coupling 17 of first part 15 as in FIG. 2. The method has the step of receiving the coded signals before activating or deactivating the source of high frequency energy 12 with switch 23 coupled to memory 25 in the identifying circuit 22 wherein the memory 25 compares the coded signals to predetermined instrument 11 identification therein. The method has the step of communicating through optical couplings 17 and 18 by non contact, coded proximity detectors responsive to diffuse surface invisible infrared optical energy for instrument 11 identification.

The qualifying connection 10 for instrument 11 in a preferred embodiment attaches to source of high frequency energy 12 for electrosurgery. Surgical signals from the source of high frequency energy 12 are delivered through qualifying connection 10 to and from instrument 11. First part 15 couples to instrument 11 and second part 16 is in the source of high frequency energy 12. Mechanical attachments 20 and 21 on first and second parts 15 and 16 geometrically conjugate. The mechanical attachments 20 and 21 extend across the qualifying connection 10 for juxtapositioning first and second parts 15 and 16. Mechanical attachments 21 on second part 16 connect to source of high frequency energy 12. Mechanical attachment 20 on first part 15 couples to instrument 11 for delivery of high frequency energy 12 and therefore are electrical conductors. Optical couplings 17 and 18 on first and second parts 15 and 16 pass invisible optical energy thereacross to communicate instrument 11 identity. Optical couplings 17 and 18 geographically orient proximate relative to the juxtaposed first and second parts 15 and 16 for communicating when the mechanical attachments 20 and 21 conjugate. Infrared light supply 19 in source of high frequency energy 12, connects through optical couplings 17 and 18 in the transmission across the communicating optical couplings 17 and 18. Infrared light modifier 24 on optical coupling 17 is positioned proximal for coding of the transmitted infrared light communicated there across.

Cable 27 fitted between first part 15 and instrument 11 carries high frequency energy from mechanical attachments 20 and 21 to instrument 11. Cable 27 allows movement of instrument 11 relative to source of high frequency energy 12. Identifying circuit 22 in source of high frequency energy 12 connects to respond to infrared light optically coded by infrared light modifier 24. Identifying circuit 22 verifies the type of instrument 11 connected by cable 27 through qualifying connection 10 to source of high frequency 12 electrosurgical energy. Identifying circuit 22 connects for signaling the verification to source of high frequency energy 12.

Switch 23 in source of high frequency energy 12 couples to identifying circuit 22 for responding to the signals of identifying circuit 22. Switch 23 connected within source of high frequency energy 12 for enabling and disabling the flow of high frequency energy 12 therefrom and through at least one of mechanical attachments 20 and 21, cable 27 and to the instrument 11.

One form qualifying connection 10 includes first part 15 thereof connected to instrument 11 and second part 16 thereof carried in and connected to source of medical treatment 12. A transmitter such as light supply 19 on source of medical treatment 12 delivers informational energy to first part 15 on instrument 11 and modifier 24 on first part 15 is proximately positioned relative to transmitter 19. Modifier 24 changes the energy from the transmitter 19. One or more receivers such as detectors 26 on second part 16 are located for receipt of the changed energy from modifier 24. Mechanical attachments 20 and 21 across qualifying connection 10 juxtaposition first and second parts 15 and 16 thereof. Mechanical attachments 20 and 21 having geometric conjugations deliver medical treatment through qualifying connection 10 from source of medical treatment 12 to instrument 11. Mechanical attachments 20 and 21 position proximally and geographically first part 15 on instrument 11 and second part 16 on source of medical treatment 12 when mechanical attachments 20 and 21 conjugate so that first and second parts 15 and 16 may communicate across qualifying connection 10 between first and second parts 15 and 16 for transmitting and receiving information and modified energy thereacross thus communicating the identity of instrument 11 to and medical treatment from source of medical treatment 12.

Identifying circuit 22 connects to second part 16 located in source of medical treatment 12 for receiving communicated information from receiver 26. Identifying circuit 22 responds to communicated information for differentiating the type of instrument 11 connected by mechanical attachments 20 and 21 through qualifying connection 10 to source of medical treatment 12. Identifying circuit 22 generates a signal of verification to source of medical treatment 12. Switch 23 in source of medical treatment 12 responds to the signaling of identifying circuit 22. Switch 23 connects to identifying circuit 22 within source of medical treatment 12. Switch 23 connects within source of medical treatment 12 for controlling the passage of medical treatment from source of medical treatment 12 through at least one of the mechanical attachments 20 or 21 and to instrument 11.

Switch 23 is connected to an energy provider such as an electrosurgical generator in source of medical treatment 12. Switch 23 within identifier circuit 22 communicates identification information to allow setting the nature of the energy conveyed in accord with instrument 11 identified and for differentiating instrument 11 attached through qualifying connection 10 from other unqualified instruments 11. Transmitter 19 delivers light in the infrared wavelengths and the modifier 24 is preferably a surface on first part 15 positioned proximal to transmitter 19 on second part 16. The surface is configured to modify the delivered light by absorption, diffraction, reflection or a combination thereof. Mechanical attachments 20 and 21 preferrable include one or more electrical conductors and the energy provider includes the electrosurgical generator for delivery of modes of radio frequency electrosurgery across the mechanical attachments 20 and 21. Mechanical attachments 20 and 21 include alternatively one or more wave guides when the energy provider is a laser for delivery of light energy through mechanical attachments 20 and 21. Mechanical attachments 20 and 21 include alternatively one or more fluid passages when the energy provider is a fluid movement apparatus for delivery of suction or irrigation through the mechanical attachments 20 and 21. Mechanical attachments 20 and 21 include alternatively one or more energy couplings when the energy provider is a microwave generator for delivery of microwaves through the mechanical attachments 20 and 21. The mechanical attachment 20 and 21 include alternatively male and female portions.

Modifier 24 is located in first part 15 sandwiched between the transmitter 19 and receiver 26 on second part 16. The surface includes matrix 28 for modifying the light in the infrared wavelengths. The receivers 26 may include fiber optics extending between second part 16 and the source of medical treatment 12, detectors located in source of medical treatment 12 connected to the fiber optics so that the space required for the detectors is uninhibited by second part 16. The receivers may include fiber optics extending between second part 16 and source of medical treatment 12. The fiber optics have several groups of multiple redundant fibers for simultaneously passage of the information from modifier 24 in the form of modified light. A plurality of cells such as optical coupling are within source of medical treatment 12 so each group of the multiple redundant fibers may extend to a particular cell and deliver thereto modified light as coded identity information.

The preferred embodiment of the smart recognition system has a smart qualifying connector 10 bipolar jack, smart sense processor, an illuminating display indicator that validates instrument 11 recognition, and a medical instrument. There is a mating plug and surgical instrument 11, attached by a connective cable. The medical instrument plug may establish an Nth bit code identity. The smart connector bipolar jack is preferably located on the front panel of the electrosurgical generator. The bipolar jack is preferably the power receptacle through which the electrosurgical generator outputs the Rf energy to an attached medical instrument. Rf energy output can only occur after the smart recognition identity of the medical instrument has been correctly established. Physical configuration of the connector is preferably asymmetric to allow a unidirectional attachment of the medical instrument. This conditional mating, automatically facilitates the proper orientation of the medical instrument plug, so that the infrared proximity detectors can properly decode the medical instrument identity. The bipolar jack is most preferably manufactured from a machined piece of black polymer. This creates a shrouded, dark adaptive, light environment for the infrared sensory components, to recover the maximum signal. The black polymer absorbs the unwanted infrared light, if any, in the operating room and is opaque to visible light preventing reflection, transmission and pickup by the smart sense components.

A rectangular cutout, present in the bipolar jack, may allow the infrared components, mounted on the smart sense processor a viewing aperture window for inspection of the mated medical instrument plug. The identification and verification of compatibility for electrosurgical use results. The smart sense processor mounted on top of the bipolar jack performs the function of coded proximity detection using diffuse surface infrared reflective coupling to the attached medical instrument plug. An Nth bit signal code unique to the instrument 11 attached is recovered. Upon retrieving the medical instrument identity, the information is hardware and software processed to discriminate if the identity code is correct. Discrimination is made to determine if the attached instrument 11 should be supplied Rf energy from the electrosurgical generator. Considering a valid recognition, Rf energy is delivered to a tissue site for surgical use. The smart sensing performs hardware code processing. The smart processor either locally controls the activation of the Rf energy of the generator or transmits the code information to a microcontroller wherein a comparative decision is made relative to the instrument 11 identity.

A display indicator provides visual illumination of a positive bit code recognition, that the correct medical instrument 11 is attached to the electrosurgical generator. The display is located on the front panel of the electrosurgical generator. Display illumination continues as long as the identity of the attached medical instrument is recognized. Removal of the medical instrument plug deactivates the display indicator and prevents any further keyed activation of Rf energy, from the generator output.

The medical instrument has a mating connection and instrument with a connective cable. The plug is preferably an overmolded assembly with pin contacts that mate with a bipolar jack receptacle on the generator for transferring the Rf energy. A matrix of holes and plugs is established between the molded plug and receptacle. The holes and plugs permit infrared light therethrough or reflected to establish the Nth bit identity code unique to the medical instrument. Exposure of the plug to liquids should not ordinarily alter the identity code of the instrument 11. Fluids entering this matrix of holes will pass by gravity due to the vertical orientation of the preferred embodiment of the holes. Fluids present on the plug surface, in the area occupied by the plug insert, should not alter the retrieval process of the identity code, due to the proximity detection by infrared sensors. The unfocused infrared optical sensor responds to the presence of objects with irregular surfaces.

Diffraction of light energy due to surface granularity or discontinuities should not contribute significantly to the loss of signal recovered by the infrared sensor. The proximity of the infrared sensor does not obviate the recovery of code information due to adjacent bit cell sites. A rapid fall off the diffractive light energy prevents the corruption of the unique identity code. The accuracy and integrity of the smart recognition system for electrosurgery are preserved.

The medical instrument plug inserts are used to establish the Nth bit code identity for the instrument 11 and are located in the overmolded plug. These plug inserts are constructed of compatible materials to the plug and are fitted and arranged consistent with the identity code selected. The arrangement permits retrieval by the proximity detection method described.

While a particular preferred embodiment has been illustrated and described, the scope of protection sought in the claims that follow covers any connection that uses non environmental radiation across an optical coupling to verify or identify the instrument 11 connected before energy is permitted to pass through the connection from the high frequency generator to the instrument 11.

In addition to the preferred embodiment, which uses non contact, coded proximity identity detection with diffuse surface reflection optical coupling, the scope of claims delineated herein covers enhancements to optical couplings and coding methods with alternate light modifiers and light conduits. This includes as example alternate light modification technology methods using light modulation or matrix encoding methods to generate unique coding algorithms. The use of fiber optics as a light conduit may enhance code identity detection methods with multiple redundant fibers used in specific cell structure orientations so information transmitted provides a unique light discriminator to the diffuse reflection light in the infrared wavelengths. Alternate configurations which strategically reposition the transmitters, receivers and light modifiers to further enhance the coded proximity detection means are in the claims for optimal optical coupling.

What is claimed is:

1. A qualifying connection for a smart recognition apparatus for identifying a type of surgical instrument attached to a surgical generator, said qualifying connection comprising:

first and second parts, said first part adapted to be attached to the surgical instrument and said second part adapted to be attached to the surgical generator, said first part having at least one mechanical interface disposed thereon for selectively engaging at least one corresponding mechanical interface disposed on the second part;

first and second optical couplings disposed between said first and second parts, respectively, said first and second optical couplings optically aligning when said mechanical interfaces of said first and second parts are mechanically engaged, said first and second optical couplings when optically aligned communicating identifying information to an identifying circuit which verifies the type of surgical instrument attached to the generator.

2. A qualifying connection according to claim 1 wherein said identifying circuit communicates with the generator to regulate the electrosurgical energy to the surgical instrument based upon the type of surgical instrument identified by the identifying circuit.

3. A qualifying connection according to claim 2 further comprising a switch for controlling the electrosurgical energy to the surgical instrument in response to signals from the identifying circuit.

4. A qualifying connection according to claim 1 wherein the optical coupling on the first part includes a light modifier which modifies the radiation of the light for thereafter receipt by the optical coupling on the second part, the modified radiation of light being indicative of the type of surgical instrument connected to the first part.

5. A qualifying connection according to claim 1 wherein infrared transmitters are positioned on the second part proximal the light modifier for optical communication of the light therethrough.

6. A qualifying connection according to claim 1 wherein the light modifier of the optical coupling on the first part includes one of a diffuse surface, a coating, a matrix of apertures and a pre-selective light responsive material.

7. A qualifying connection according to claim 4 wherein the optical coupling of the second part includes at least one light transmitter and the light modifier on the first part alters the optical energy transmitted from the at least one transmitter.

8. A qualifying connection according to claim 1 wherein the identifying circuit includes a memory for controlling the activation or deactivation of electrosurgical energy according a predetermined criteria for the type of instrument identified.

9. A qualifying connection according to claim 1 further comprising a display indicator which provides visual feedback as to the type and mechanical mating integrity of the surgical instrument attached to the generator.

10. A qualifying connection according to claim 1 wherein at least one of the mechanical interfaces of the first part and the corresponding mechanical interface on the second part include fluid passages for delivering one of suction and irrigation to the surgical instrument.

11. A qualifying connection according to claim 1 wherein the qualifying connection communicates treatment information from the surgical instrument through at least one of the optical couplings regarding the status of tissue being treated.

12. A qualifying connection according to claim 1 wherein the qualifying connection communicates parametric information from the surgical instrument through at least one of the optical couplings regarding at least one of tissue temperature, thermal spread, tissue eschar and tissue desiccation.

* * * * *